(12) United States Patent
Brown et al.

(10) Patent No.: US 8,609,931 B2
(45) Date of Patent: Dec. 17, 2013

(54) POLYPEPTIDES HAVING BETA-GLUCOSIDASE ACTIVITY AND POLYNUCLEOTIDES ENCODING SAME

(75) Inventors: Kimberly Brown, Elk Grove, CA (US); Paul Harris, Carnation, WA (US)

(73) Assignee: Novozymes, Inc., Davis, CA (US)

( * ) Notice: Subject to any disclaimer, the term of this patent is extended or adjusted under 35 U.S.C. 154(b) by 400 days.

(21) Appl. No.: 12/886,244

(22) Filed: Sep. 20, 2010

(65) Prior Publication Data
US 2011/0072540 A1 Mar. 24, 2011

Related U.S. Application Data

(60) Provisional application No. 61/243,532, filed on Sep. 18, 2009.

(51) Int. Cl.
| C12N 15/56 | (2006.01) |
| C12N 15/82 | (2006.01) |
| C12N 9/42  | (2006.01) |
| C12P 21/02 | (2006.01) |

(52) U.S. Cl.
USPC .......... 800/284; 800/298; 435/200; 435/71.1; 536/23.2; 424/93.2

(58) Field of Classification Search
None
See application file for complete search history.

(56) References Cited

U.S. PATENT DOCUMENTS

| 4,243,752 A | 1/1981 | Skinner et al. |
| 2007/0238155 A1* | 10/2007 | Gusakov et al. ............ 435/101 |
| 2008/0201805 A1* | 8/2008 | Krogh et al. ................ 800/298 |
| 2009/0042266 A1 | 2/2009 | Vehmaanpera et al. |

FOREIGN PATENT DOCUMENTS

| WO | WO 2009/018537 | 2/2009 |
| WO | WO 2009/073723 | 6/2009 |
| WO | WO 2009073723 A1 * | 6/2009 |

OTHER PUBLICATIONS

Berka et al. 2011. Comparative genomic analysis of the thermophilic biomass-degrading fungi *Myceliophthora thermophilia* and *Thielavia terrestris*. Nature. 29(10):922-929.*
Berka et al. 2011 (as stated above) Supplementary Data and Figures, pp. 1-46).*
Guo et al. 2004. Protein tolerance to random amino acid change. PNAS. 101(25):9205-9210.*
Himmel et al. 2007. Biomass recalcitrance: Engineering plants and enzymes for biofuels production. Science. 315:804-807.*
Pozzo et al. 2010. Structural and functional analyses of beta-glucosidase 3B from *Thermotoga neapolitana*: A thermostable three-domain representative of glycoside hydrolase 3. J Mol Biol. 397:724-739.*
Bukhtojarov et al. 2004. Cellulase complex of the fungus *Chrysosporium lucknowense*: Isolation and characterization of endoglucanases and cellobiohydrolases. Biochemistry (Moscow). 69(5):542-551.*
Alapuranen, M., US 2009 042266—Access No. AWH58324.
Gosink, M., WO 2009-018537—Access No. AWH29250.

* cited by examiner

Primary Examiner — Anne Kubelik
Assistant Examiner — Jeffrey Bolland
(74) Attorney, Agent, or Firm — Robert L. Starnes

(57) ABSTRACT

The present invention relates to isolated polypeptides having beta-glucosidase activity and isolated polynucleotides encoding the polypeptides. The invention also relates to nucleic acid constructs, vectors, and host cells comprising the polynucleotides as well as methods of producing and using the polypeptides.

22 Claims, 3 Drawing Sheets

```
         M  K  P  A  I  V  L  S  S  L  A  C  S  G  L  A  A  A  S  A  V  S
   1 ATGAAGCCTGCCATTGTGCTTTCCAGCCTGGCCTGCAGCGGTCTTGCTGCCGCCAGTGCGGTCAGC
         S  S  D  K
  67 TCGTCGGACAAGgtatggttaacttgcaggttccgtcgcattcgtctcccccttcattcccccttt
 133 ttcccttctcccgccgttgcagcgaaggctgcgagagtccattcattggaccctcttgttttattt
 199 tccgttccaagcatcgcccgggaagttcacccgctgccaagattcgctttagccagattggcgagc
 265 ccgttgcgcgttgcaacccgctcccgccatgcggctcagatctgcggctcaatggctcctcgtgct
                                                        P  L  E  K  R  T  L  A
 331 cccggcgagaagcagcggtcttgctgacaaaaactcccaccagCCGCTTGAGAAAAGGACACTCGC
       T  S  E  P  F  Y  P  S  P  W  M  N  P  D  A  D  G  W  T  E  A  Y
 397 AACGTCGGAACCTTTCTACCCGTCGCCATGGATGAACCCGGACGCCGACGGTTGGACCGAGGCCTA
       A  R  A  K  E  F  V  S  R  M  T  L  L  E  K  V  N  L  T  T  G  V
 463 TGCCCGCGCTAAGGAGTTCGTCTCCCGGATGACGCTGCTGGAGAAGGTCAACCTGACCACGGGGGT
       G                                                             W  E
 529 TGGGgtaagtgcgaaccgggcctgggaccgtggaatgcgagctgtgctgatcgtcctgcagCTGGGA
       A  E  Q  C  V  G  Q  V  G  A  I  P  R  L  G  R  S  L  C  M  Q
 595 GGCGGAGCAGTGCGTCGGCCAGGTGGGCGCCATTCCTCGCCTGGGCCTGCGGAGCTTGTGCATGCA
       D  S  P  L  G  V  R  G  T  D  F  N  S  G  F  P  S  G  Q  T  A  A
 661 GGACTCTCCGCTCGGTGTCCGGGGACCGACTTCAACTCCGGGTTCCCTTCCGGCCAGACGGCGGC
       A  T  F  D  R  G  L  I  Y  R  R  G  Y  A  M  G  Q  E  A  R  G  K
 727 CGCCACCTTCGATCGCGGCCTGATCTACCGGCGCGGCTATGCCATGGGCCAGGAGGCCAGGGGCAA
       G  V  N  V  L  L  G  P  V  A  G  P  L  G  R  A  P  T  G  G  R  N
 793 GGGAGTCAATGTCCTGCTCGGACCTGTTGCCGGCCCCCTTGGACGTGCCCCTACCGGCGGTCGGAA
       W  E  G  F  S  P  D  P  V  L  T  G  V  G  M  A  E  S  I  K  G  I
 859 CTGGGAAGGGTTCTCCCCTGACCCTGTTCTCACCGGCGTGGGCATGGCCGAGTCCATCAAGGGCAT
       Q  D  A  G  T  I  A  C  A  K  H  F  I  G  N  E  Q
 925 CCAAGACGCCGGCACGATTGCTTGTGCGAAGCACTttattggcaacgagcaaggtgagccgcgatt
                                                        E  H  F  R  Q  V
 991 gcagtcccggggctttccgagaggaagaacgtgctaacagacgtgcagAGCACTTCAGGCAAGTGG
       G  E  A  Q  G  Y  G  F  N  I  S  E  A  L  S  S  N  I  D  D  K  T
1057 GGGAGGCGCAAGGTTACGGGTTCAACATCAGCGAGGCCCTGTCGTCCAACATTGACGACAAGACCC
       L  H  E  L  Y  L  W  P  F  A  D  A  V  R  A  G  V  G  S  V  M  C
1123 TGCACGAGCTCTACCTCTGGCCGTTTGCGGACGCCGTGAGGGCCGGCGTCGGCTCCGTCATGTGCT
       S  Y  Q  Q  L  N  N  S  Y  S  C  Q  N  S  K  L  L  N  G  L  L  K
1189 CGTACCAGCAGCTCAACAACTCGTACAGCTGCCAGAACTCCAAGCTCCTGAATGGCCTGCTCAAGG
       G  E  L  G  F  Q  G  F  V  M  S  D  W  Q  A  Q  H  T  G  A  A  S
1255 GCGAACTCGGTTTCCAGGGCTTCGTCATGAGCGATTGGCAGGCCCAGCACACGGGCGCCGCAAGCG
       A  V  A  G  L  D  M  T  M  P  G  D  T  E  F  N  T  G  R  S  Y  W
1321 CTGTTGCCGGCCTCGACATGACCATGCCGGGAGACACCGAGTTCAACACGGGCCGGAGCTACTGGG
       G  A  N  L  T  L  A  V  L  N  G  T  V  P  A  Y  R  I  D  D  M  A
1387 GCGCCAACCTGACGCTCGCGGTGCTCAACGGCACCGTCCCCGCCTACCGCATCGACGACATGGCCA
       M  R  I  M  A  A  F  F  K  V  N  K  D  I  K  L  D  P  I  N  F  S
1453 TGCGCATCATGGCCGCCTTCTTCAAGGTCAACAAGGACATCAAGCTGGACCCCATCAACTTCTCCT
       F  W  T  L  D  T  Y  G  P  I  H  W  A  A  Q  T  G  Y  Q  Q  I  N
1519 TCTGGACCCTGGACACGTACGGCCCGATTCACTGGGCGGCGCAGACGGGCTACCAGCAGATCAACT
       Y  H  V  D  V  R  A  D  H  G  S  L  I  R  E  I  G  A  K  G  T  V
1585 ACCACGTGGATGTGCGAGCCGACCACGGCAGCCTTATCCGGGAGATCGGCGCCAAGGGAACCGTGC
       L  L  K  N  T  G  S  L  P  L  K  K  P  K  F  L  A  V  I  G  E  D
1651 TCCTCAAGAACACCGGCTCTCTGCCCTTGAAGAAGCCGAAATTCCTGGCCGTGATTGGCGAGGACG
       A  G  P  N  T  S  G  P  N  S  C  S  D  R  G  C  D  N  G  T  L  A
1717 CCGGCCCCAACACCAGCGGGCCGAACTCTTGCTCCGACAGGGGATGTGACAATGGCACTCTCGCCA
       M  G  W  G  S  G  T  A  N  F  P  Y  V  V  T  P  D  A  A  L  Q  A
1783 TGGGCTGGGGTTCCGGCACCGCCAACTTCCCGTACGTCGTCACGCCCGATGCCGCGCTGCAGGCGC
       Q  A  L  Q  D  G  S  R  Y  E  S  I  L  S  N  Y  A  T  S  Q  I  K
1849 AGGCCCTCCAGGACGGTTCGCGCTACGAGAGCATCCTGTCCAACTATGCGACATCGCAAATAAAGG
       A  L  V  S  Q  A  N  V  T  A  I  V  F  V  N  A  D  S  G  E  G  Y
1915 CTCTTGTGTCACAAGCCAACGTGACAGCAATCGTCTTTGTCAACGCCGACTCGGGCGAGGGCTACA
```

FIG. 1A

```
              I   N   V   D   G   N   M   G   D   R   K   N   L   T   L   W   K   D   G   D   A   L
1981 TCAATGTGGACGGAAACATGGGCGACCGGAAGAACCTGACGCTGTGGAAGGATGGCGACGCGCTGG
          V   K   N   V   A   S   W   C   S   N   T   I   V   V   I   H   S   P   G   P   V   L
2047 TCAAGAACGTGGCCAGCTGGTGCTCCAACACCATCGTCGTGATCCATTCCCCGGGCCCGGTTCTGC
          L   T   E   W   Y   N   S   P   N   V   T   A   I   L   W   A   G   L   P   G   Q   E
2113 TGACCGAGTGGTACAACAGCCCCAACGTTACCGCTATCCTCTGGGCCGGTCTCCCCGGCCAAGAGT
          S   G   N   S   I   A   D   V   L   Y   G   R   V   N   P   A   A   R   S   P   F   T
2179 CCGGCAACTCGATCGCCGACGTTCTGTACGGCAGGGTCAACCCTGCCGCGCGGTCGCCGTTCACGT
          W   G   P   T   R   E   S   Y   G   T   D   V   L   Y   T   P   N   N   G   N   G   A
2245 GGGGCCCAACCCGCGAGAGTTACGGGACCGATGTTCTCTACACGCCGAACAACGGCAACGGCGCGC
          P   Q   D   D   F   T   E   G   V   F   I   D   Y   R   Y   F   D   K   T   N   S   S
2311 CGCAGGACGACTTCACCGAGGGCGTCTTCATCGACTACCGCTACTTTGACAAGACCAACTCGTCCG
          V   I   Y   E   F   G   H   G   L   S   Y   T   T   F   E   Y   S   N   I   R   V   Q
2377 TCATTTACGAGTTCGGCCACGGCCTCAGCTACACCACGTTTGAGTACAGCAACATCCGGGTACAGA
          K   S   N   A   G   K   Y   E   P   T   T   G   K   T   S   P   A   P   T   F   G   N
2443 AGTCGAACGCGGGCAAGTACGAGCCCACGACGGGCAAGACCTCGCCCGCGCCCACCTTTGGCAACT
          F   S   T   N   L   K   D   Y   V   F   P   S   H   E   F   P   Y   V   Y   E   Y   I
2509 TCTCGACCAACCTCAAAGACTACGTGTTCCCGAGCCACGAGTTCCCTTACGTTTACGAGTACATCT
          Y   P   Y   L   N   T   T   D   P   K   A   A   S   G   D   A   N   Y   G   Q   T   A
2575 ATCCTTACCTCAACACGACCGACCCCAAGGCGGCCTCGGGCGACGCGAACTACGGCCAGACGGCCG
          D   K   F   L   P   P   H   A   T   D   S   S   A   Q   P   L   L   R   S   S   G   K
2641 ACAAGTTCCTCCCGCCGCACGCGACCGACTCGTCGGCCCAGCCGCTGCTGCGCTCGTCGGGCAAGA
          N   S   P   G   G   N   R   Q   L   Y   D   V   M   Y   T   I   T   A   D   I   K   N
2707 ACTCGCCGGGCGGCAACCGGCAGTTGTACGACGTCATGTACACGATCACGGCCGACATCAAGAACA
          T   G   S   I   V   G   E   E   V   P   Q   L   Y   V   A   L   G   G   P   D   D   P
2773 CGGGCTCGATCGTCGGCGAGGAGGTGCCGCAGCTGTACGTCGCGCTGGGCGGGCCGGACGACCCCA
          K   V   Q   L   R   D   F   D   R   I   R   I   D   P   G   K   T   A   Q   F   R   G
2839 AGGTGCAGCTGCGCGACTTTGACCGCATCCGCATCGACCCGGGCAAGACGGCGCAGTTCCGCGGCA
          T   L   T   R   R   D   L   S   N   W   D   T   T   L   Q   D   W   V   I   S   K   Y
2905 CGCTGACCCGCAGGGACCTGAGCAACTGGGATACGACGCTGCAGGACTGGGTCATTAGCAAGTACA
          K   K   T   A   Y   V   G   R   S   S   R   K   L   D   L   S   I   E   L   P   *
2971 AGAAGACGGCGTATGTGGGGAGGAGCAGCCGGAAGCTGGACTTGAGCATTGAGTTGCCGTGA
```

POLYPEPTIDES HAVING BETA-GLUCOSIDASE ACTIVITY AND POLYNUCLEOTIDES ENCODING SAME

CROSS-REFERENCE TO RELATED APPLICATIONS

This application claims the benefit of U.S. Provisional Application No. 61/243,532, filed Sep. 18, 2009, which application is incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

1. Field of the Invention

The present invention relates to polypeptides having beta-glucosidase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

There is a need in the art for polypeptides having beta-glucosidase activity with improved properties for use in the degradation of cellulosic materials.

The present invention provides polypeptides having beta-glucosidase activity and polynucleotides encoding the polypeptides.

SUMMARY OF THE INVENTION

The present invention relates to isolated polypeptides having beta-glucosidase activity selected from the group consisting of:

(a) a polypeptide having at least 81% sequence identity to the mature polypeptide of SEQ ID NO: 2;

(b) a polypeptide encoded by a polynucleotide that hybridizes under high or very high stringency conditions with (i) the mature polypeptide coding sequence of SEQ ID NO: 1, (ii) the cDNA sequence contained in the mature polypeptide coding sequence of SEQ ID NO: 1 or (iii) the full-length complementary strand of (i) or (ii);

(c) a polypeptide encoded by a polynucleotide having at least 81% sequence identity to the mature polypeptide coding sequence of SEQ ID NO: 1 or the cDNA sequence thereof;

(d) a variant comprising a substitution, deletion, and/or insertion of one or more (several) amino acids of the mature polypeptide of SEQ ID NO: 2; and (e) a fragment of the polypeptide of (a), (b), (c), or (d) that has beta-glucosidase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to methods for degrading or converting a cellulosic material, comprising: treating the cellulosic material with an enzyme composition in the presence of a polypeptide having beta-glucosidase activity of the present invention.

The present invention also relates to methods of producing a fermentation product, comprising: (a) saccharifying a cellulosic material with an enzyme composition in the presence of a polypeptide having beta-glucosidase activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having beta-glucosidase activity of the present invention.

The present invention also relates to a polynucleotide encoding a signal peptide comprising or consisting of amino acids 1 to 18 of SEQ ID NO: 2, which is operably linked to a gene encoding a protein; nucleic acid constructs, expression vectors, and recombinant host cells comprising the polynucleotide; and methods of producing a protein.

BRIEF DESCRIPTION OF THE FIGURES

FIGS. 1A and 1B shows the genomic DNA sequence and the deduced amino acid sequence of a gene encoding a _Thielavia terrestris_ NRRL 8126 GH3B polypeptide having beta-glucosidase activity (SEQ ID NOs: 1 and 2, respectively).

DEFINITIONS

Figure 2:
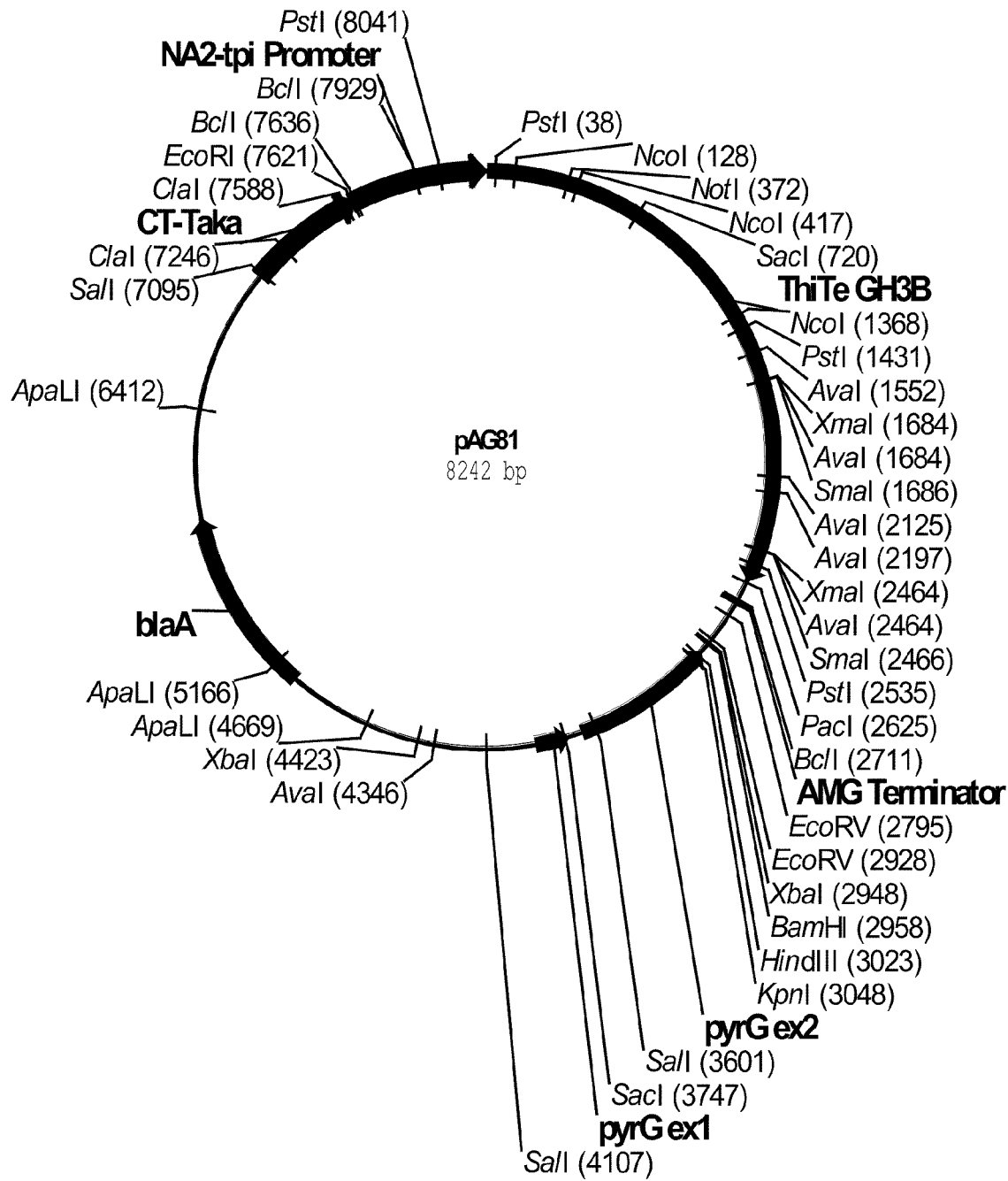
FIG. 2 shows a restriction map pAG81.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from _Chaetomium thermophilum_ var. _coprophilum_: production, purification and some biochemical properties, _J. Basic Microbiol._ 42: 55-66. One unit of beta-glucosidase is defined as 1.0 μmole of p-nitrophenolate anion produced per minute at pH 5, 40° C. from 1 mM p-nitrophenyl-beta-D-glucopyranoside as substrate in 100 mM sodium acetate containing 0.01% TWEEN® 20. In another aspect, beta-glucosidase activity is determined using cellobiose as substrate. One unit of beta-glucosidase is defined as the amount of enzyme capable of releasing 1 μmole of glucose per minute at pH 5, 50° C. from 4 mM cellobiose as substrate in in 50 mM sodium acetate buffer of pH 5.0 containing 0.01% TWEEN® 20.

Cellulolytic enzyme or cellulase: The term "cellulolytic enzyme" or "cellulase" means one or more (several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, Biotechnology Advances 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, Pure Appl. Chem. 59: 257-68).

For purposes of the present invention, cellulolytic enzyme activity is determined by measuring the increase in hydrolysis of a cellulosic material by cellulolytic enzyme(s) under the following conditions: 1-20 mg of cellulolytic enzyme protein/g of cellulose in PCS for 3-7 days at 50° C. compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, Biotechnology Advances 24: 452-481). For purposes of the present invention, endoglucanase activity is determined using carboxymethyl cellulose (CMC) as substrate according to the procedure of Ghose, 1987, Pure and Appl. Chem. 59: 257-268, at pH 5, 40° C.

Cellobiohydrolase: The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, Trends in Biotechnology 15: 160-167; Teeri et al., 1998, Trichoderma reesei cellobiohydrolases: why so efficient on crystalline cellulose?, Biochem. Soc. Trans. 26: 173-178). For purposes of the present invention, cellobiohydrolase activity is determined according to the procedures described by Lever et al., 1972, Anal. Biochem. 47: 273-279; van Tilbeurgh et al., 1982, FEBS Letters, 149: 152-156; van Tilbeurgh and Claeyssens, 1985, FEBS Letters, 187: 283-288; and Tomme et al., 1988, Eur. J. Biochem. 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-β-D-lactoside.

Polypeptide having cellulolytic enhancing activity: The term "polypeptide having cellulolytic enhancing activity" means a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight Aspergillus oryzae beta-glucosidase (recombinantly produced in Aspergillus oryzae according to WO 02/095014) or 2-3% of total protein weight Aspergillus fumigatus beta-glucosidase (recombinantly produced in Aspergillus oryzae as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Family 3 or 61 glycoside hydrolase: The term "Family 3 glycoside hydrolase" or "Family GH3" or "GH3" or "Family 61 glycoside hydrolase" or "Family GH61" or "GH61" means a polypeptide falling into the glycoside hydrolase Family 3 or Family 61 according to Henrissat B., 1991, A classification of glycosyl hydrolases based on amino-acid sequence similarities, Biochem. J. 280: 309-316, and Henrissat B., and Bairoch A., 1996, Updating the sequence-based classification of glycosyl hydrolases, Biochem. J. 316: 695-696.

Hemicellulolytic enzyme or hemicellulase: The term "hemicellulolytic enzyme" or "hemicellulase" means one or more (several) enzymes that hydrolyze a hemicellulosic material. See, for example, Shallom, D. and Shoham, Y. Microbial hemicellulases. Current Opinion In Microbiology, 2003, 6(3): 219-228). Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum* commune, *FEBS Letters* 580 (19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 µmole of p-nitrophenolate anion per minute at pH 5, 25° C.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methyl-glucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose, which comprises cellulose, hemicellulose, and lignin.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Isolated or Purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 872 of SEQ ID NO: 2 based on the SignalP program (Nielsen et al., 1997, *Protein Engineering* 10:1-6) that predicts amino acids 1 to 18 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having beta-glucosidase activity. In one aspect, the mature polypeptide coding sequence is nucleotides 55 to 3029 of SEQ ID NO: 1 based on the SignalP program (Nielsen et al., 1997, supra) that predicts nucleotides 1 to 54 of SEQ ID NO: 1 encode a signal peptide. In another aspect, the mature polypeptide coding sequence is the cDNA sequence contained in nucleotides 55 to 3029 of SEQ ID NO: 1.

Sequence Identity The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has beta-glucosidase activity. In one aspect, a fragment contains at least 720 amino acid residues, e.g., at least 760 amino acid residues or at least 800 amino acid residues of SEQ ID NO: 2.

Subsequence: The term "subsequence" means a polynucleotide having one or more (several) nucleotides deleted from the 5' and/or 3' end of a mature polypeptide coding sequence; wherein the subsequence encodes a fragment having beta-glucosidase activity. In one aspect, a subsequence contains at least 2160 nucleotides, e.g., at least 2280 nucleotides or at least 2400 nucleotides of SEQ ID NO: 1.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having beta-glucosidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding one or more (several) amino acids, e.g., 1-5 amino acids, adjacent to an amino acid occupying a position.

DETAILED DESCRIPTION OF THE INVENTION

Polypeptides Having Beta-Glucosidase Activity

The present invention relates to isolated polypeptides having beta-glucosidase activity selected from the group consisting of:

(a) a polypeptide having at least 81% sequence identity to the mature polypeptide of SEQ ID NO: 2;

(b) a polypeptide encoded by a polynucleotide that hybridizes under high or very high stringency conditions with (i) the mature polypeptide coding sequence of SEQ ID NO: 1, (ii) the cDNA sequence contained in the mature polypeptide coding sequence of SEQ ID NO: 1, or (iii) the full-length complementary strand of (i) or (ii);

(c) a polypeptide encoded by a polynucleotide having at least 81% sequence identity to the mature polypeptide coding sequence of SEQ ID NO: 1; or the cDNA sequence thereof;

(d) a variant comprising a substitution, deletion, and/or insertion of one or more (several) amino acids of the mature polypeptide of SEQ ID NO: 2; and (f) a fragment of a polypeptide of (a), (b), (c), or (d) that has beta-glucosidase activity.

The present invention relates to isolated polypeptides having a sequence identity to the mature polypeptide of SEQ ID NO: 2 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have beta-glucosidase activity. In one aspect, the polypeptides differ by no more than ten amino acids, e.g., by five amino acids, by four amino acids, by three amino acids, by two amino acids, and by one amino acid from the mature polypeptide of SEQ ID NO: 2.

A polypeptide of the present invention preferably comprises or consists of the amino acid sequence of SEQ ID NO: 2 or an allelic variant thereof; or is a fragment thereof having beta-glucosidase activity. In another aspect, the polypeptide comprises or consists of the mature polypeptide of SEQ ID NO: 2. In another preferred aspect, the polypeptide comprises or consists of amino acids 19 to 872 of SEQ ID NO: 2.

The present invention also relates to isolated polypeptides having beta-glucosidase activity that are encoded by polynucleotides that hybridize under high stringency conditions or very high stringency conditions with (i) the mature polypeptide coding sequence of SEQ ID NO: 1, (ii) the cDNA sequence contained in the mature polypeptide coding sequence of SEQ ID NO: 1, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1, or a subsequence thereof, as well as the amino acid sequence of SEQ ID NO: 2, or a fragment thereof, may be used to design nucleic acid probes to identify and clone DNA encoding polypeptides having beta-glucosidase activity from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having beta-glucosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the polynucleotide hybridizes to a labeled nucleic acid probe corresponding to SEQ ID NO: 1; the mature polypeptide coding sequence of SEQ ID NO: 1; the cDNA sequence contained in the mature polypeptide coding sequence of SEQ ID NO: 1; the full-length complementary strands thereof; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1, or the cDNA sequence thereof. In another aspect, the nucleic acid probe is nucleotides 55 to 3029 of SEQ ID NO: 1. In another aspect, the nucleic acid probe is a polynucleotide that encodes the polypeptide of SEQ ID NO: 2, or the mature polypeptides thereof; or fragments thereof. In another preferred aspect, the nucleic acid probe is SEQ ID NO: 1, or the cDNA sequence thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$, using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to isolated polypeptides having beta-glucosidase activity encoded by polynucleotides having a sequence identity to the mature polypeptide coding sequence of SEQ ID NO: 1, or the cDNA sequence thereof, of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The present invention also relates to variants comprising a substitution, deletion, and/or insertion of one or more (or several) amino acids of the mature polypeptide of SEQ ID NO: 2, or homologous sequences thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for beta-glucosidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2 is not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Beta-Glucosidase Activity

A polypeptide having beta-glucosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a Bacillus, Clostridium, Enterococcus, Geobacillus, Lactobacillus, Lactococcus, Oceanobacillus, Staphylococcus, Streptococcus, or Streptomyces polypeptide having beta-glucosidase activity, or a gram-negative bacterial polypeptide such as a Campylobacter, E. coli, Flavobacterium, Fusobacterium, Helicobacter, Ilyobacter, Neisseria, Pseudomonas, Salmonella, or Ureaplasma polypeptide.

In one aspect, the polypeptide is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis polypeptide.

In another aspect, the polypeptide is a Streptococcus equisimilis, Streptococcus pyogenes, Streptococcus uberis, or Streptococcus equi subsp. Zooepidemicus polypeptide.

In another aspect, the polypeptide is a Streptomyces achromogenes, Streptomyces avermitilis, Streptomyces coelicolor, Streptomyces griseus, or Streptomyces lividans polypeptide.

The polypeptide may also be a fungal polypeptide. For example, the polypeptide may be a yeast polypeptide such as a Candida, Kluyveromyces, Pichia, Saccharomyces, Schizosaccharomyces, or Yarrowia polypeptide; or a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Trichoderma harzianum, Trichoderma koningii, Trichoderma longibrachiatum, Trichoderma reesei*, or *Trichoderma viride* polypeptide.

In another aspect, the polypeptide is a *Thielavia terrestris* polypeptide having beta-glucosidase activity. In another aspect, the polypeptide is a *Thielavia terrestris* NRRL 8126 polypeptide having beta-glucosidase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Thielavia terrestris*, or a related organism and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1, or the cDNA sequence thereof, of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encode a polypeptide having beta-glucosidase activity.

Modification of a polynucleotide encoding a polypeptide of the present invention may be necessary for the synthesis of polypeptides substantially similar to the polypeptide. The term "substantially similar" to the polypeptide refers to nonnaturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under high stringency conditions or very high stringency conditions with (i) the mature polypeptide coding sequence of SEQ ID NO: 1, (ii) the cDNA sequence contained in the mature polypeptide coding sequence of SEQ ID NO: 1, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1 or the mature polypeptide coding sequence of SEQ ID NO: 1, or a subsequence of SEQ ID NO: 1 that encodes a fragment of SEQ ID NO: 2 having beta-glucosidase activity, such as the polynucleotide of nucleotides 55 to 3029 of SEQ ID NO: 1.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American*, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in *Aspergilli* in which the untranslated leader has been replaced by an untranslated leader from a gene encoding triose phosphate isomerase in *Aspergilli*; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus* equi subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Thielavia*. In a more preferred aspect, the cell is *Thielavia terrestris*. In a most preferred aspect, the cell is *Thielavia terrestris* NRRL 8126.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, cotransformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Removal or Reduction of Beta-Glucosidase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In a particularly preferred aspect, the polynucleotide is disrupted with a selectable marker such as those described herein.

The present invention also relates to methods of inhibiting the expression of a polypeptide having beta-glucosidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for the expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially beta-glucosidase activity, beta-xylosidase activity, or beta-glucosidase and beta-xylosidase-free product is of particular interest in the production of eukaryotic polypeptides, in particular fungal proteins such as enzymes. The beta-glucosidase activity, beta-xylosidase activity, or beta-glucosidase and beta-xylosidase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-glucosidase activity that is produced by a method of the present invention.

Compositions

The present invention also relates to compositions comprising a polypeptide of the present invention. Preferably, the compositions are enriched in such a polypeptide. The term "enriched" indicates that the beta-glucosidase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (several) enzymes selected from the group consisting of a cellulase, a hemicellulase, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following methods for using the polypeptides having beta-glucosidase activity, or compositions thereof.

The present invention also relates to methods for degrading or converting a cellulosic material, comprising: treating the cellulosic material with an enzyme composition in the presence of a polypeptide having beta-glucosidase activity of the present invention. In one aspect, the method further comprises recovering the degraded or converted cellulosic material. Soluble products of degradation or conversion of the cellulosic material can be separated from the insoluble cellulosic material using technology well known in the art such as, for example, centrifugation, filtration, and gravity settling.

The present invention also relates to methods of producing a fermentation product, comprising: (a) saccharifying a cellulosic material with an enzyme composition in the presence of a polypeptide having beta-glucosidase activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having beta-glucosidase activity of the present invention. In one aspect, the fermenting of the cellulosic material produces a fermentation product. In another aspect, the method further comprises recovering the fermentation product from the fermentation.

The methods of the present invention can be used to saccharify the cellulosic material to fermentable sugars and convert the fermentable sugars to many useful substances, e.g., fuel, potable ethanol, and/or fermentation products (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate process steps to first enzymatically hydrolyze the cellulosic material to fermentable sugars, e.g., glucose, cellobiose, cellotriose, and pentose sugars, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components of the cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment: In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from the cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having beta-glucosidase activity of the present invention. The enzymes of the compositions can be added sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The enzyme compositions can comprise any protein that is useful in degrading or converting the cellulosic material.

In one aspect, the enzyme composition comprises or further comprises one or more (several) proteins selected from the group consisting of a cellulase, a polypeptide having cellulolytic enhancing activity, a hemicellulase, an expansin, an esterase, a laccase, a ligninolytic enzyme, a pectinase, a peroxidase, a protease, and a swollenin. In another aspect, the cellulase is preferably one or more (several) enzymes selected from the group consisting of an endoglucanase, a cellobiohydrolase, and a beta-glucosidase. In another aspect, the hemicellulase is preferably one or more (several) enzymes selected from the group consisting of an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (several) cellulolytic enzymes. In another aspect, the enzyme composition comprises or further comprises one or more (several) hemicellulolytic enzymes. In another aspect, the enzyme composition comprises one or more (several) cellulolytic enzymes and one or more (several) hemicellulolytic enzymes. In another aspect, the enzyme composition comprises one or more (several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity. In another aspect, the enzyme composition comprises an acetylmannan esterase. In another aspect, the enzyme composition comprises an acetyxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase). In another aspect, the enzyme composition comprises an expansin. In another aspect, the enzyme composition comprises an esterase. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the methods of the present invention, the enzyme(s) can be added prior to or during fermentation, e.g., during saccharification or during or after propagation of the fermenting microorganism(s).

One or more (several) components of the enzyme composition may be wild-type proteins, recombinant proteins, or a combination of wild-type proteins and recombinant proteins. For example, one or more (several) components may be native proteins of a cell, which is used as a host cell to express recombinantly one or more (several) other components of the enzyme composition. One or more (several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having beta-glucosidase activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In a preferred aspect, an effective amount of cellulolytic enzyme to the cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of the cellulosic material.

In another preferred aspect, an effective amount of a polypeptide having beta-glucosidase activity to the cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of the cellulosic material.

In another preferred aspect, an effective amount of a polypeptide having beta-glucosidase activity to cellulolytic enzyme is about 0.005 to about 1.0 g, preferably about 0.01 to about 1.0 g, more preferably about 0.15 to about 0.75 g, more preferably about 0.15 to about 0.5 g, more preferably about 0.1 to about 0.5 g, even more preferably about 0.1 to about 0.25 g, and most preferably about 0.05 to about 0.2 g per g of cellulolytic enzyme.

The polypeptides having cellulolytic enzyme activity or hemicellulolytic enzyme activity as well as other proteins/polypeptides useful in the degradation of the cellulosic material, e.g., polypeptides having cellulolytic enhancing activity (hereinafter "polypeptides having enzyme activity") can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another preferred aspect, the polypeptide is a *Streptococcus equisimilis, Streptococcus pyogenes, Streptococcus uberis*, or *Streptococcus equi* subsp. *Zooepidemicus* polypeptide having enzyme activity.

In another preferred aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus* niger, *Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention include, but are not limited to, a *Trichoderma reesei* endoglucanase I (Penttila et al., 1986, *Gene* 45: 253-263; *Trichoderma reesei* Cel7B endoglucanase I; GENBANK™ accession no. M15665); *Trichoderma reesei* endoglucanase II (Saloheimo, et al., 1988, *Gene* 63:11-22; *Trichoderma reesei* Cel5A endoglucanase II; GENBANK™ accession no. M19373); *Trichoderma reesei* endoglucanase III (Okada et al., 1988, *Appl. Environ. Microbiol.* 64: 555-563; GENBANK™ accession no. AB003694); *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase; *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the present invention include, but are not limited to, *Trichoderma reesei* cellobiohydrolase I; *Trichoderma reesei* cellobiohydrolase II; *Humicola insolens* cellobiohydrolase I; *Myceliophthora thermophila* cellobiohydrolase II; *Thielavia terrestris* cellobiohydrolase II (CEL6A); *Chaetomium thermophilum* cellobiohydrolase I; and *Chaetomium thermophilum* cellobiohydrolase II.

Examples of beta-glucosidases useful in the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

In the methods of the present invention, any GH61 polypeptide having cellulolytic enhancing activity can be used.

In a first aspect, the polypeptide having cellulolytic enhancing activity comprises the following motifs:

[ILMV]-P-X(4,5)-G-X-Y-[ILMV]-X-R-X-[EQ]-X(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The polypeptide comprising the above-noted motifs may further comprise:

H-X(1,2)-G-P-X(3)-[YW]-[AILMV], [EQ]-X-Y-X(2)-C-X-[EHQN]-[FILV]-X-[ILV], or H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the polypeptide having cellulolytic enhancing activity further comprises H-X(1,2)-G-P-X(3)-[YW]-[AILMV]. In another preferred aspect, the isolated polypeptide having cellulolytic enhancing activity further comprises [EQ]-X-Y-X(2)-C-X-[EHQN]-[FILV]-X-[ILV]. In another preferred aspect, the polypeptide having cellulolytic enhancing activity further comprises H-X(1,2)-G-P-X(3)-[YW]-[AILMV] and [EQ]-X-Y-X(2)-C-X-[EHQN]-[FILV]-X-[ILV].

In a second aspect, the polypeptide having cellulolytic enhancing activity comprises the following motif:

[ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of polypeptides having cellulolytic enhancing activity useful in the methods of the present invention include, but are not limited to, polypeptides having cellulolytic enhancing activity from *Thielavia terrestris* (WO 2005/074647); polypeptides having cellulolytic enhancing activity from *Thermoascus aurantiacus* (WO 2005/074656); polypeptides having cellulolytic enhancing activity from *Trichoderma reesei* (WO 2007/089290); and polypeptides having cellulolytic enhancing activity from *Myceliophthora thermophila* (WO 2009/085935; WO 2009/085859; WO 2009/085864; WO 2009/085868).

In one aspect, the one or more (several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8x212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number Q0UHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8x211), *Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is (are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as some yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum*, *Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another more preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis*, *Clostridium acetobutylicum*, *Clostridium thermocellum*, *Chlostridium phytofermentans*, *Geobacillus* sp., Thermoanaerobacter saccharolyticum, and *Bacillus coagulans* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (Fermentis/Lesaffre, USA), FALI™ (Fleischmann's Yeast, USA), SUPERSTART™ and THERMOSACC™ fresh yeast (Ethanol Technology, WI, USA), BIOFERM™ AFT and XR (NABC—North American Bioproducts Corporation, GA, USA), GERT STRAND™ (Gert Strand AB, Sweden), and FERMIOL™ (DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo- D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 18 of SEQ ID NO: 2. The polynucleotide may further comprise a gene encoding a protein, which is operably linked to the signal peptide. The protein is preferably foreign to the signal peptide.

The present invention also relates to nucleic acid constructs, expression vectors and recombinant host cells comprising such a polynucleotide.

The present invention also relates to methods of producing a protein, comprising: (a) cultivating a recombinant host cell comprising such a polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Thielavia terrestris* NRRL 8126 was used as the source of a Family 3 polypeptide having beta-glucosidase activity.

Media

PDA plates were composed of 39 g of potato dextrose agar and distilled water to 1 liter.

NNCYP medium was composed of 5.0 g of $NaNO_3$, 3.0 g of $NH_4Cl$, 2.0 g of MES, 2.5 g of citric acid, 0.2 g of $CaCl_2 2H_2O$, 1.0 g of Bacto Peptone, 5.0 g of yeast extract, 0.2 g of $MgSO_4 7H_2O$, 4.0 g of $K_2HPO_4$, 1.0 ml of COVE trace elements solution, 2.5 g of glucose, and distilled water to 1 liter.

COVE trace elements solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and distilled water to 1 liter.

MY50 medium was composed of 50 g of Maltodextrin, 2 g of MgSO47H20, 10 g of KH2PO4, 2 g of K2SO4, 2 g of citric acid, 10 g of yeast extract, 2 g of urea, 0.5 ml of AMG trace metals solution, and distilled water to 1 liter.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, 3 g of citric acid, and distilled water to 1 liter.

50× Vogels medium was composed per liter of 150 g of sodium citrate, 250 g of $KH_2PO_4$, 10 g of $MgSO_4.7H_2O$, 10 g of CaCl$_2$.2H$_2$O, 2.5 ml of biotin stock solution, 5.0 ml of AMG trace metals solution, and distilled water to 1 liter.

LB plates were composed of 10 g of Bacto-tryptone. 5 g of yeast extract, 10 g of sodium chloride, 15 g of agar, and distilled water to 1 liter.

LB medium was composed of 10 g of Bacto-tryptone. 5 g of yeast extract, 10 g of sodium chloride, and distilled water to 1 liter.

Example 1

Peptide Sequencing by Tandem Mass Spectrometry of a Polypeptide Encoding a Family 3 Beta-Glucosidase from *Thielavia terrestris* NRRL 8126

Three agarose plugs from culture of *Thielavia terrestris* NRRL 8126 grown on a PDA plate were inoculated into 100 ml of NNCYP medium supplemented with 1.5% glucose and incubated for 25 hours at 42° C. and 200 rpm on an orbital shaker. Fifty ml of this culture was used to inoculate 1.8 liter of NNCYP medium supplemented with 0.4% glucose and 52 g of powdered cellulose per liter and was incubated at 42° C. The pH was controlled at 5.0 by the addition of 15% ammonium hydroxide or 5 N phosphoric acid, as needed.

The fermentations were run at 42° C. with minimum dissolved oxygen at 25% at a 1.0 VVM air flow and an agitation at 1100 rpm. Feed medium was delivered into a 2 liter fermentation vessel at 0 hours with a feed rate of 6.0-8.0 g/hour for 120 hours. Pooled cultures were centrifuged at 3000×g for 10 minutes and the supernatant was filtered through a disposable filtering unit with a glass fiber prefilter (Nalgene, Rochester N.Y., USA). The filtrate was cooled to 4° C. for storage.

A 0.3 ml aliquot of the filtrate was precipitated with 10% trichloroacetic acid (TCA)-80% acetone for 20 minutes on ice. The suspension was centrifuged for 10 minutes at 13,000×g. The supernatant was removed and the protein pellet remaining was rinsed with cold acetone. The protein pellet was dissolved in 30 μl of 1× lithium dodecyl sulfate (LDS) SDS-PAGE loading buffer with 50 mM dithiothreitol (DTT) and heated at 80° C. for 10 minutes. A 15 μl sample was separated by SDS-PAGE using a 7 cm 4-12% NuPAGE Bis-Tris SDS-PAGE gradient gel and 2-(N-morpholino)ethanesulfonic acid (MES) running buffer. The SDS-PAGE was run under reducing conditions according to the manufacturer's recommended protocol (Invitrogen, Carlsbad, Calif., USA). The gel was removed from the cassette and rinsed 3 times with deionized water for at least 5 minutes each and stained with Bio-Safe Coomassie Stain (Bio-Rad Laboratories, Inc., Hercules, Calif., USA) for 1 hour followed by destaining with doubly-distilled water for more than 30 minutes. Protein bands observed at approximately 95 kD was excised and reduced with 50 μl of 10 mM DTT in 100 mM ammonium bicarbonate for 30 minutes. Following reduction, the gel pieces were alkylated with 50 μl of 55 mM iodoacetamide in 100 mM ammonium bicarbonate for 20 minutes. The dried gel pieces were allowed to re-hydrate in a trypsin digestion solution (6 ng/μl sequencing grade trypsin in 50 mM ammonium bicarbonate) for 30 minutes at room temperature, followed by an 8 hour digestion at 40° C. Each of the reaction steps described was followed by numerous washes and pre-washes with the desired solutions. Fifty μl of acetonitrile was used to de-hydrate the gel pieces between reactions and they were air-dried between steps. Peptides were extracted twice with 1% formic acid/2% acetonitrile in HPLC grade water for 30 minutes. Peptide extraction solutions were transferred to a 96 well PCR type microtiter plate that had been cooled to 10-15° C. Microtiter plates containing the recovered peptide solutions were sealed to prevent evaporation and stored at 4° C. until mass spectrometry analysis could be performed.

For de-novo peptide sequencing by tandem mass spectrometry, a Q-Tof Micro™, a hybrid orthogonal quadrupole time-of-flight mass spectrometer (Waters Micromass® MS Technologies, Milford, Mass., USA) was used for LC/MS/MS analysis. The Q-Tof Micro™ was fitted with an Ultimate™ capillary and nano-flow HPLC system which had been coupled with a FAMOS micro autosampler and a Switchos II column switching device (LCPackings, San Francisco, Calif., USA) for concentrating and desalting samples. Samples were loaded onto a guard column (300 μm ID×5 cm, C18 pepmap) fitted in the injection loop and washed with 0.1% formic acid in water at 40 μl/minute for 2 minutes using the Switchos II pump. Peptides were separated on a 75 μm ID×15 cm, C18, 3 μm, 100 Å PepMap™ (LC Packings, San Francisco, Calif., USA) nanoflow fused capillary column at a flow rate of 175 nl/minute from a split flow of 175 μl/minute using a NAN-75 calibrator (Dionex, Sunnyvale, Calif., USA). A step elution gradient of 5% to 80% acetonitrile in 0.1% formic acid was applied over a 45 minute interval. The column eluent was monitored at 215 nm and introduced into the Q-Tof Micro™ through an electrospray ion source fitted with the nanospray interface. The Q-Tof Micro™ is fully microprocessor controlled using Masslynx™ software version 3.5 (Waters Micromass® MS Technologies, Milford, Mass., USA). Data was acquired in survey scan mode and from a mass range of m/z 400 to 1990 with the switching criteria for MS to MS/MS to include an ion intensity of greater than 10.0 counts per second and charge states of +2, +3, and +4. Analysis spectra of up to 4 co-eluting species with a scan time of 1.9 seconds and inter-scan time of 0.1 seconds could be obtained. A cone voltage of 65 volts was typically used and the collision energy was programmed to be varied according to the mass and charge state of the eluting peptide and in the range of 10-60 volts. The acquired spectra were combined, smoothed and centered in an automated fashion and a peak list generated. This peak list was searched against selected public and private databases using ProteinLynx™ Global Server 1.1 software (Waters Micromass® MS Technologies, Milford, Mass.). Results from the ProteinLynx™ searches were evaluated and un-identified proteins were analyzed further by evaluating the MS/MS spectrums of each ion of interest and de-novo sequence was determined by identifying the y and b ion series and matching mass differences to the appropriate amino acid.

Peptide sequences obtained from de novo sequencing by mass spectrometry were obtained from several multiply charged ions for the approximately 95 kDa polypeptide gel band.

A doubly charged tryptic peptide ion of 524.76 m/z sequence was determined to be Ser-Pro-Phe-Thr-Trp-Gly-Pro-Thr-Arg (amino acids 607 to 615 of SEQ ID NO: 2). A second doubly charged tryptic peptide ion of 709.91 partial sequence was determined to be Gly-Val-Asn-Val-[Ile/Leu]-[Ile-Leu]-Gly-[Ile/Leu]-Gly-Pro (amino acids 148 to 155 of SEQ ID NO: 2). A second doubly charged tryptic peptide ion of 745.38 partial sequence was determined to be Pro-Pro-His-Ala-Thr-Asp (amino acids 747 to 752 of SEQ ID NO: 2). A third doubly charged tryptic peptide ion of 808.92 m/z sequence was determined to be Tyr-Glu-Ser-[Ile/Leu]-[Ile/Leu]-Ser-Asn-Tyr-Ala-Thr-Ser-Qln-[Ile/Leu]-Lys (amino acids 487 to 499 of SEQ ID NO: 2). A fourth doubly charged tryptic peptide ion of 1023.96 a partial sequence was determined to be Phe-Asn-Ser-Gly-Phe-Pro-Ser-Gly-Gln-Thr-Ala-Ala-Ala-Thr-Phe-Asp-Arg (amino acids 114 to 130 of SEQ ID NO: 2).

Example 2

Thielavia terrestris NRRL 8126 Genomic DNA Extraction

To generate genomic DNA for PCR amplification, Thielavia terrestris NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, Okla., USA) for 45 seconds in a FastPrep FP120 (ThermoSavant, Holbrook, N.Y., USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 µl of 0.1× TE and incubated with 1 µl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

Example 3

Identification of a Beta-Glucosidase Gene in the Genomic Sequence of Thielavia terrestris A low redundancy draft sequence of the Thielavia terrestris NRRL 8126 genome was generated by the Joint Genome Center (JGI), Walnut Creek, Calif., USA, using the whole genome shotgun method according to Martinez et al., 2008, Nature Biotechnol. 26: 553-560. Shotgun sequencing reads (approximately 18307) were assembled into contigs using the Phrap assembler (Ewing and Green, 1998, Genome Res. 8: 186-194).

A tblastn search (Altschul et al., 1997, Nucleic Acids Res. 25: 3389-3402) of the assembled contigs was carried out using as query a beta-glucosidase protein sequence from Neurospora crassa (UniProt accession number q7rwp2). A translated amino acid sequence with greater than 73.8% identity to the query sequence was identified.

The sequence was searched against public databases using blastp (Altschul et al., 1997, Nucleic Acids Res. 25: 3389-3402) and was found to be 80.1% identical to a beta-glucosidase from Podospora anserina (UniProt accession number B2AVE8).

The nucleotide sequence (SEQ ID NO: 1) and deduced amino acid sequence (SEQ ID NO: 2) of the Thielavia terrestris beta-glucosidase gene are shown in FIGS. 1A and 1B. The coding sequence is 3032 bp including the stop codon and is interrupted by three introns of 295 bp, 57 bp, and 61 bp. The encoded predicted protein is 872 amino acids. Using the SignalP program (Nielsen et al., 1997, Protein Engineering 10:1-6), a signal peptide of 18 residues was predicted. The predicted mature protein contains 854 amino acids with a predicted molecular mass of 93 kDa and an isoelectric point of 5.57.

A comparative pairwise global alignment of amino acid sequences was determined using the Needleman-Wunsch algorithm (Needleman and Wunsch, 1970, J. Mol. Biol. 48: 443-453) as implemented in the Needle program of EMBOSS with gap open penalty of 10, gap extension penalty of 0.5, and the EBLOSUM62 matrix. The alignment showed that the deduced amino acid sequence of the Thielavia terrestris gene encoding the polypeptide having beta-glucosidase activity shares 80.1% identity (excluding gaps) to the deduced amino acid sequence of a beta-glucosidase from Podospora anserina (UniProt accession number B2AVE8).

Example 4

Thielavia terrestris GH3B cDNA

Thielavia terrestris NRRL 8126 was grown for 3 days on PDA plates at 45° C. Mycelia were scraped from the plates and approximately 100 mg of mycelia (wet weight) were used to inoculate 500 ml shake flasks containing 100 ml of either MY50 medium or 1×Vogel's medium supplemented with 2% microcrystalline cellulose (AVICEL®). Cultures were grown for 2, 3, 4 and 5 days at 45° C. with vigorous shaking. The mycelia were harvested by filtration through MIRACLOTH® (EMD Chemicals Inc., Gibbstown, N.J., USA), and quick frozen in liquid nitrogen.

To isolate total RNA frozen mycelia of Thielavia terrestris NRRL 8126 were ground in an electric coffee grinder. The ground material was mixed 1:1 v/v with 20 ml of FENAZOL™ (Ambion, Inc., Austin, Tex., USA) in a 50 ml tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

RNA samples were pooled and the quality and quantity of the purified RNA was assessed with an AGILENT® 2100 Bioanalyzer (Agilent Technologies, Inc., Palo Alto, Calif., USA). A total of 630 µg of RNA was isolated.

Poly A+ RNA was isolated from total RNA using an Absolutely mRNA™ Purification Kit (Stratagene, La Jolla, Calif., USA) according to the manufacturer's instructions. cDNA synthesis and cloning was performed according to a procedure based on the SuperScript™ Plasmid System with Gateway® Technology for cDNA Synthesis and Cloning (Invitrogen, Carsbad, Calif., USA). 1-2 µg of poly A+ RNA, reverse transcriptase SuperScript II (Invitrogen, Carsbad, Calif., USA), and oligo dT-Not I primer 5'-GACTAGTTCTAGATCGCGAGCGGCCGCCCTTTTTTTTTTTTTTVN-3' (SEQ ID NO: 3) were used to synthesize first strand cDNA. Second strand synthesis was performed with E. coli DNA ligase, polymerase I, and RNase H followed by end repair using T4 DNA polymerase. The Sal I adaptor (5'-TCGACCCACGCGTCCG-3' [SEQ ID NO: 4] and 5'-CGGACGCGTGGG-3'[SEQ ID NO: 5]) was ligated to the cDNA, digested with Not I, and subsequently size selected (>2 kb) by 1.1% agarose gel electrophoresis using 40 mM Tris base-20 mM sodium acetate-1 mM disodium EDTA (TAE) buffer. The cDNA inserts were directionally ligated into Sal I and Not I digested vector pCMVsport6 (Invitrogen, Carsbad, Calif., USA). The ligation was transformed into ElectroMAX™ DH10B™ T1 cells (Invitrogen, Carsbad, Calif., USA).

Library quality was first assessed by randomly selecting 24 clones and PCR amplifying the cDNA inserts with the primers M13-F and M13-R shown below to determine the fraction of insertless clones.

```
Primer M13-F:
5'-GTAAAACGACGGCCAGT-3'    (SEQ iD NO: 6)

Primer M13-R:
5'-AGGAAACAGCTATGACCAT-3'  (SEQ iD NO: 7)
```

Colonies from each library were plated onto LB plates at a density of approximately 1000 colonies per plate. Plates were grown at 37° C. for 18 hours and then individual colonies were picked and each used to inoculate a well containing LB medium supplemented with 100 µg of ampicillin per ml in a 384 well plate (Nunc, Rochester, N.Y., USA). Clones were grown at 37° C. for 18 hours. Plasmid DNA for sequencing was produced by rolling circle amplification using a Templiphi™ Kit (GE Healthcare, Piscataway, N.J., USA). Subclone inserts were sequenced from both ends using primers complimentary to the flanking vector sequence as shown below and BigDye® terminator chemistry using a 3730 DNA Analyzer (Applied Biosystems, Foster City, Calif., USA).

```
Forward primer:
5'-ATTTAGGTGACACTATAGAA-3'  (SEQ iD NO: 8)

Reverse primer:
5'-TAATACGACTCACTATAGGG-3'  (SEQ iD NO: 9)
```

A clone showing 67.4% identity at the nucleotide level to a beta-glucosidase from *Aspergillus oryzae* (U.S. Published Application No. 2005233423) was identified.

Example 5

Construction of an *Aspergillus oryzae* Expression Vector for the *Thielavia terrestris* Family GH3B Gene Two synthetic oligonucleotide primers shown below were designed to PCR amplify the *Thielavia terrestris* Family GH3B beta-glucosidase gene from the cDNA clone. An IN-FUSION® Cloning Kit (BD Biosciences, Palo Alto, Calif., USA) was used to clone the fragment directly into the expression vector pAILo2 (WO 2005/074647), without the need for restriction digestion and ligation.

```
Forward primer:
                                      (SEQ ID NO: 10)
5'-ACTGGATTTACCATGAAGCCTGCCATTGTGCT-3'

Reverse primer:
                                      (SEQ ID NO: 11)
5'-TCACCTCTAGTTAATTAATCACGGCAACTCAATGCTCA-3'
```

Bold letters represent coding sequence. The remaining sequence is homologous to the insertion sites of pAILo2.

Fifty picomoles of each of the primers above were used in a PCR reaction containing 200 ng of plasmid cDNA (prepared as described in Example 4), 1× 2× Advantage GC-Melt LA Buffer (Clonetech Laboratories, Inc., Mountain View, Calif., USA), 1 µl of 10 mM blend of dATP, dTTP, dGTP, and dCTP, and 1.25 units of Advantage GC Genomic LA Polymerase Mix (Clonetech Laboratories, Inc., Mountain View, Calif., USA) in a final volume of 50 µl. The amplification was performed using an EPPENDORF® MASTERCYCLER® 5333 epgradient S (Eppendorf Scientific, Inc., Westbury, N.Y., USA) programmed for one cycle at 94° C. for 1 minute; and 30 cycles each at 94° C. for 30 seconds, 60.5° C. for 30 seconds, and 72° C. for 3 minutes. The heat block was then held at 72° C. for 15 minutes followed by a 4° C. soak cycle.

The reaction products were isolated by 1.0% agarose gel electrophoresis using TAE buffer where an approximately 2.6 kbp product band was excised from the gel and purified using a MINELUTE® Gel Extraction Kit (QIAGEN Inc., Valencia, Calif., USA) according to the manufacturer's instructions.

The fragment was then cloned into pAILo2 using an IN-FUSION® Cloning Kit. The vector was digested with Nco I and Pac I. The fragment was purified by gel electrophoresis as above and a QIAQUICK® Gel Purification Kit (QIAGEN Inc., Valencia, Calif., USA). The gene fragment and the digested vector were combined together in a reaction resulting in the expression plasmid pAG81 (FIG. 2), in which transcription of the Family GH3B protein gene was under the control of the NA2-tpi promoter (a hybrid of the promoters from the genes for *Aspergillus niger* neutral alpha-amylase and *Aspergillus nidulans* triose phosphate isomerase). The recombination reaction (10 µl) was composed of 1×IN-FUSION® Buffer (BD Biosciences, Palo Alto, Calif., USA), 1×BSA (BD Biosciences, Palo Alto, Calif., USA), 1 µl of IN-FUSION® enzyme (diluted 1:10) (BD Biosciences, Palo Alto, Calif., USA), 108 ng of pAILo2 digested with Nco I and Pac I, and 94 ng of the *Thielavia terrestris* GH3B protein purified PCR product. The reaction was incubated at 37° C. for 15 minutes followed by 15 minutes at 50° C. The reaction was diluted with 40 µl of 10 mM Tris-0.1 M EDTA buffer and 2.5 µl of the diluted reaction was used to transform *E. coli* TOP10 Competent cells (Stratagene, La Jolla, Calif., USA). An *E. coli* transformant containing pAG81 (GH3B protein gene) was identified by restriction enzyme digestion and plasmid DNA was prepared using a BIOROBOT® 9600 (QIAGEN Inc., Valencia, Calif., USA). The plasmid construct was sequenced using an Applied Biosystems 3130xl Genetic Analyzer (Applied Biosystems, Foster City, Calif., USA) to verify the gene sequence.

Example 6

Expression of the *Thielavia Terrestris* cDNA Encoding a GH3B Polypeptide Having Beta-Glucosidase Activity in *Aspergillus Oryzae* JaL355

*Aspergillus oryzae* JaL355 protoplasts were prepared according to the method of Christensen et al., 1988, *Bio/Technology* 6: 1419-1422, which were transformed with 5 µg of pAG81. Twenty-six transformants were isolated to individual PDA plates. A small plug from each transformant was used to inoculate 1 ml of M410 media in a 24 well plate and incubated at 34° C. After 5 days of incubation, 7.5 µl of supernatant from four transformants was analyzed using a CRITERION® stain-free, 8-16% gradient SDS-PAGE gel (Bio-Rad Laboratories, Inc., Hercules, Calif., USA) according to the manufacturer's instructions. SDS-PAGE profiles of the cultures showed that several transformants had a new major band of approximately 150 kDa.

A confluent PDA plate of the top transformant (was washed with 5 ml of 0.01% TWEEN® 20 and inoculated into 500 ml flasks each containing 100 ml of M410 medium to generate broth for characterization of the enzyme. The flasks were harvested on day 5, filtered using a 0.22 µm stericup suction filter (Millipore, Bedford, Mass., USA), and stored at 4° C.

Example 7

Purification of *Thielavia terrestris* Beta-Glucosidase (GH3B)

A 45 ml aliquot of shake flask broth prepared as described in Example 6 was concentrated ten-fold using a VIVASPIN™ 20 sample concentrator with a molecular weight cut-off of 10 kDa (GE Healthcare, Piscataway, N.J., USA) and buffer-exchanged into 50 mM sodium acetate of pH 5. A 4 ml aliquot of the buffer-exchanged, concentrated broth was then diluted to a 10 ml volume with 1 M Tris-HCl pH 8 and water to a concentration of 20 mM Tris-HCl, and the pH adjusted to a final value of 8 using 2 N sodium hydroxide. The resulting material was then purified using a MONO Q™ 5/5 column (GE Healthcare, Piscataway, N.J., USA) equilibrated with 20 mM Tris-HCl buffer pH 7.8. Unbound material was washed from the column with 2 ml equilibration buffer, and then the column was eluted with a linear gradient from 0-500 mM sodium chloride in the equilibration buffer. Fractions of 0.3 ml were collected. Unbound material collected during column loading and unbound material washed from the column were pooled for a total volume of 12 ml. Five µl of the fractions, including the pooled unbound material, showing UV absorbance at 280 nm were analyzed using a CRITERION STAIN FREE™ 8-16% Tris-HCl SDS-PAGE gel (Bio-Rad Laboratories, Inc., Hercules, Calif., USA) according to the manufacturer's instructions. Precision Plus Protein™ unstained standards (Bio-Rad Laboratories, Inc., Hercules, Calif., USA) were used as molecular weight markers. The gel was removed from the cassette and imaged using a CRITERION STAIN FREE™ IMAGER (Bio-Rad Laboratories, Inc., Hercules, Calif., USA). The beta-glucosidase was identified in the pooled unbound material as a band at 150 kDa by SDS-PAGE. The 12 ml of pooled unbound material was concentrated as described above to a final volume of 2 ml. The concentrated material was purified using a HILOAD™ 16/60 SUPERDEX™ 75 PREP GRADE column (GE Healthcare, Piscataway, N.J., USA) equilibrated with 20 mM Tris.HCl buffer of pH 7.8 containing 150 mM sodium chloride, and eluted with the equilibration buffer. Fractions of 3 ml were collected. Column fractions were analyzed by SDS-PAGE as described above. Fractions containing the purified beta-glucosidase, identified by a band at 150 kDa by SDS-PAGE, were pooled for a total volume of 6 ml. The pooled material was concentrated using a VIVASPIN™ 6 sample concentrator with a molecular weight cut-off of 5 kDa (GE Healthcare, Piscataway, N.J., USA) to a final volume of 0.4 ml. Protein concentration was determined using the Bio-Rad Protein Assay (Bio-Rad Laboratories, Inc., Hercules, Calif., USA).

The enzyme activity of the purified beta-glucosidase was measured using p-nitrophenyl-beta-D-glucopyranoside as substrate. A p-nitrophenyl-beta-D-glucopyranoside stock solution was made by dissolving p-nitrophenyl-beta-D-glucopyranoside in dimethylsulfoxide (DMSO) to constitute a 0.1 M solution. Before assay, a sample of the stock solution was diluted 100-fold in 100 mM sodium acetate pH 5 containing 0.01% TWEEN® 20 to a 1 mM solution. A 100 µl volume of 1 mM p-nitrophenyl-beta-D-glucopyranoside was mixed with each dilution of the enzyme for a 120 µl total volume, and then incubated at 40° C. for 20 minutes. Substrate alone, enzyme alone, and buffer alone were run as controls. p-Nitrophenol standard solutions of 0.40, 0.25, 0.20, 0.10, 0.05, and 0.02 mM were prepared by diluting a 10 mM stock solution in 100 mM sodium acetate pH 5 containing 0.01% TWEEN® 20. At 20 minutes, 50 µl of 1.0 M sodium carbonate buffer pH 10 was added to each well (including samples, substrate control, enzyme control, reagent control, and standards), mixed, and the absorbance at 405 nm immediately measured on a SPECTRAMAX™ 340 PC plate reader (Molecular Devices, Sunnyvale, Calif., USA). The activity measured was 84 units per mg of protein. One unit of activity was defined as the amount of enzyme capable of releasing 1 µmole of p-nitrophenolate anion per minute at pH 5, 40° C.

The enzyme activity of the purified beta-glucosidase was also measured with cellobiose. A 2 mg/ml stock solution of cellobiose was prepared in 50 mM sodium acetate pH 5 containing 0.01% TWEEN® 20, and 100 µl were combined with each enzyme dilution for a total volume of 150 µl and incubated at 50° C. for 30 minutes. Substrate alone, enzyme alone, and buffer alone were run as controls. Glucose standard solutions of 1.0, 0.50, 0.25, 0.125, 0.063, and 0.031 mg/ml were prepared in 50 mM sodium acetate pH 5. containing 0.01% TWEEN® 20. At 30 minutes, 50 µl of 0.5 M sodium hydroxide solution was added to each well (including samples, substrate control, enzyme control, reagent control, and standards), mixed, and then 20 µl of the mixture was transferred to a Costar® EIA/RIA 96-well plate (Corning Incorporated, Corning, N.Y., USA) and combined with 200 µl of GLUCOSE OXIDASE REAGENT (Pointe Scientific, Inc., Canton, Mich., USA), and allowed to stand at 25° C. for 20 minutes and then the absorbance at 500 nm was measured on a SPECTRAMAX™ 340 PC plate reader (Molecular Devices, Sunnyvale, Calif., USA). The activity measured was 264 units per mg of protein. One unit of activity was defined as the amount of enzyme capable of releasing 1 µmole of glucose per minute at pH 5, 50° C.

Example 8

Sequencing of Recombinantly Expressed *Thielavia terrestris* Beta-Glucosidase

Ten µl of the purified beta-glucosidase from Example 7 was separated on a CRITERION™ 8-16% Tris-HCl SDS-PAGE gel according to the manufacturer's suggested conditions (Bio-Rad Laboratories, Inc., Hercules, Calif., USA). Precision Plus protein standards (Bio-Rad Laboratories, Inc., Hercules, Calif., USA) were used for molecular weight markers. The gel was stained with Coomassie Blue (G250) protein stain (BIO-SAFE™ Coomassie Stain, Bio-Rad Laboratories, Inc., Hercules, Calif., USA). A single 150 kDa protein band was observed and excised with a razor blade for protein identification analysis by tandem mass spectrometry. The protein band was digested with trypsin as described in Example 1 and recovered peptides were subjected to de novo peptide sequencing.

For de novo peptide sequencing by tandem mass spectrometry, a Synapt™ MS, a hybrid orthogonal quadrupole time-of-flight mass spectrometer (Waters Corp, Milford, Mass., USA) was used for the LC-MS/MS analysis. The SYNAPT™ MS is fully microprocessor controlled using MASSLYNX™ software version 4.1 (Waters Corp., Milford, Mass., USA). The SYNAPT™ MS was fitted with a NANOACQUITY UPLC® (Waters Corp, Milford, Mass., USA) for concentrating and desalting samples. Samples were loaded onto a trapping column (180 µm ID×20 mm, 5 µm SYMMETRY® C18) (Waters Corp, Milford, Mass., USA) fitted in the injection loop and washed with 0.1% formic acid in water at 15 µl per minute for 1 minutes using the binary solvent manager pump. Peptides were separated on a 100 μm ID×100 mm, C18, 1.7 μm, BEH130™ C18 nanoflow fused capillary column (Waters Corp, Milford, Mass., USA) at a flow rate of 400 nl/minute. A step elution gradient of 1% to 85% acetonitrile in 0.1% formic acid was applied over a 40 minute interval. The column eluent was monitored at 214 nm and introduced into the SYNAPT™ through an electrospray ion source fitted with the nanospray interface.

Data was acquired in survey scan mode as described in Example 1 except for the cone voltage was 45 volts and up to 6 co-eluting peptide ions could be detected. The acquired spectra were combined, smoothed, and centered in an automated fashion and a peak list generated. The peak list was searched against selected databases using PROTEINLYNX GLOBAL SERVER™ 2.4 software (Waters Corp., Milford, Mass., USA) and Mascot Daemon v. 2.2 (Matrix Sciences, London, UK) with the following settings: Peptide charge of +1, +2, +3, peptide and ms/ms tolerance were both set at 0.3 Daltons, fixed modifications were set to detect carbamidomethyl cysteine and variable modifications were set to detect oxidation of methionines. The results of the peptide mass fingerprint search results matched the protein sequence of the *Thielavia terrestris* beta-glucosidase SEQ ID NO: 2 with a mascot score of 1400 and overall sequence coverage of 32%.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide having beta-glucosidase activity, selected from the group consisting of:
    (a) a polypeptide comprising an amino acid sequence having at least 95% sequence identity to amino acids 19 to 872 of SEQ ID NO: 2;
    (b) a polypeptide encoded by a polynucleotide that hybridizes under very high stringency conditions with (i) nucleotides 55 to 3029 of SEQ ID NO: 1, (ii) a cDNA sequence of nucleotides 55 to 3029 of SEQ ID NO: 1, or (iii) a full-length complement of (i) or (ii); and
    (c) a polypeptide encoded by a polynucleotide comprising a nucleotide sequence having at least 99% sequence identity to nucleotides 55 to 3029 of SEQ ID NO:1 or a cDNA sequence thereof.

2. The polypeptide of claim 1, comprising amino acids 19 to 872 of SEQ ID NO: 2; or a fragment thereof having beta-glucosidase activity.

3. The polypeptide of claim 2, comprising amino acids 19 to 872 of SEQ ID NO: 2.

4. An isolated recombinant host cell comprising an isolated polynucleotide comprising a nucleotide sequence that encodes the polypeptide of claim 1.

5. A method of producing the polypeptide of claim 1, said method comprising: (a) cultivating an isolated Thielavia terrestris cell under conditions conducive for production of the polypeptide; and (b) recovering the polypeptide.

6. A method of producing the polypeptide of claim 1, comprising: (a) cultivating a recombinant host cell comprising an isolated polynucleotide encoding the polypeptide under conditions conducive for production of the polypeptide; and (b) recovering the polypeptide.

7. A method of producing the polypeptide of claim 1, said method comprising: (a) cultivating a transgenic plant or a plant cell comprising an isolated polynucleotide encoding the polypeptide under conditions conducive for production of the polypeptide; and (b) recovering the polypeptide.

8. A transgenic plant, plant part or plant cell transformed with a polynucleotide encoding the polypeptide of claim 1, wherein the polypeptide comprises a signal peptide directing the polypeptide into the secretory pathway.

9. A DNA construct comprising a nucleic acid encoding the signal peptide comprising or consisting of amino acids 1 to 18 of SEQ ID NO: 2 operably linked to a heterologous nucleic acid.

10. A method of producing a protein, said method comprising: (1) cultivating a recombinant host cell comprising the construct of claim 9 under conditions conducive for production of the protein; and (b) recovering the protein.

11. A method for degrading or converting a cellulosic material comprising treating the cellulosic material with an enzyme composition in the presence of the polypeptide having beta-glucosidase activity of claim 1.

12. The method of claim 11, further comprising recovering the degraded cellulosic material.

13. The method of claim 12, wherein the degraded cellulosic material is a sugar.

14. A method for producing a fermentation product, said method comprising: (a) saccharifying a cellulosic material with an enzyme composition in the presence of the polypeptide having beta-glucosidase activity of claim 1; (b) fermenting the saccharified cellulosic material with one or more fermenting microorganisms to produce the fermentation product; and (c) recovering the fermentation product from the fermentation.

15. A method of fermenting a cellulosic material comprising fermenting the cellulosic material with one or more fermenting microorganisms, wherein the cellulosic material is saccharified with an enzyme composition in the presence of the polypeptide having beta-glucosidase activity of claim 1.

16. The method of claim 15, wherein the fermenting of the cellulosic material produces a fermentation product.

17. The method of claim 16, further comprising recovering the fermentation product from the fermentation.

18. The polypeptide of claim 1, comprising an amino acid sequence having at least 96% sequence identity to amino acids 19 to 872 of SEQ ID NO: 2.

19. The polypeptide of claim 1, which is encoded by a polynucleotide comprising a nucleotide sequence having at least 99% sequence identity to nucleotides 55 to 3029 of SEQ ID NO: 1 or the cDNA sequence thereof.

20. The polypeptide of claim 18, comprising an amino acid sequence having at least 97% sequence identity to amino acids 19 to 872 of SEQ ID NO: 2.

21. The polypeptide of claim 20, comprising an amino acid sequence having at least 98% sequence identity to amino acids 19 to 872 of SEQ ID NO: 2.

22. The polypeptide of claim 21, comprising an amino acid sequence having at least 99% sequence identity to amino acids 19 to 872 of SEQ ID NO: 2.

* * * * *

```
                        SEQUENCE LISTING

<160> NUMBER OF SEQ ID NOS: 11

<210> SEQ ID NO 1
<211> LENGTH: 3032
<212> TYPE: DNA
<213> ORGANISM: Thielavia terrestris

<400> SEQUENCE: 1
atgaagcctg ccattgtgct ttccagcctg gcctgcagcg gtcttgctgc cgccagtgcg      60
gtcagctcgt cggacaaggt atggttaact tgcaggttcc gtcgcattcg tctccccctt     120
cattccccct ttttcccttc tcccgccgtt gcagcgaagg ctgcgagagt ccattcattg     180
gaccctcttg ttttattttc cgttccaagc atcgcccggg aagttcaccc gctgccaaga     240
ttcgctttag ccagattggc gagcccgttg cgcgttgcaa cccgctcccg ccatgcggct     300
cagatctgcg gctcaatggc tcctcgtgct cccggcgaga agcagcggtc ttgctgacaa     360
aaactcccac cagccgcttg agaaaaggac actcgcaacg tcggaacctt tctacccgtc     420
gccatggatg aacccggacg ccgacggttg gaccgaggcc tatgcccgcg ctaaggagtt     480
cgtctcccgg atgacgctgc tggagaaggt caacctgacc acgggggttg ggtaagtgcg     540
aaccgggcct gggaccgtgg aatgcgagct gtgctgatcg tcctgcagct gggaggcgga     600
gcagtgcgtc ggccaggtgg gcgccattcc tcgcctgggc ctgcggagct tgtgcatgca     660
ggactctccg ctcggtgtcc gggggaccga cttcaactcc gggttcctt ccggccagac     720 ggcggccgcc accttcgatc gcggcctgat ctaccgcgc ggctatgcca tgggccagga     780
ggccaggggc aagggagtca atgtcctgct cggacctgtt gccggccccc ttggacgtgc     840
ccctaccggc ggtcggaact gggaagggtt ctcccctgac cctgttctca ccggcgtggg     900
catggccgag tccatcaagg gcatccaaga cgccggcacg attgcttgtg cgaagcactt     960
tattggcaac gagcaaggtg agccgcgatt gcagtcccgg ggctttccga gaggaagaac    1020
gtgctaacag acgtgcagag cacttcaggc aagtggggga ggcgcaaggt tacgggttca    1080
acatcagcga ggccctgtcg tccaacattg acgacaagac cctgcacgag ctctacctct    1140
ggccgtttgc ggacgccgtg agggccggcg tcggctccgt catgtgctcg taccagcagc    1200
tcaacaactc gtacagctgc cagaactcca agctcctgaa tggcctgctc aagggcgaac    1260
tcggtttcca gggcttcgtc atgagcgatt ggcaggccca gcacacgggc gccgcaagcg    1320
ctgttgccgg cctcgacatg accatgccgg gagacaccga gttcaacacg ggccggagct    1380
```

```
actggggcgc caacctgacg ctcgcggtgc tcaacggcac cgtccccgcc taccgcatcg   1440
acgacatggc catgcgcatc atggccgcct tcttcaaggt caacaaggac atcaagctgg   1500
accccatcaa cttctccttc tggaccctgg acacgtacgg cccgattcac tgggcggcgc   1560
agacgggcta ccagcagatc aactaccacg tggatgtgcg agccgaccac ggcagcctta   1620
tccgggagat cggcgccaag gaaccgtgtc cctcaagaa caccggctct ctgcccttga   1680
agaagccgaa attcctggcc gtgattggcg aggacgccgg cccaacacc agcgggccga   1740 actcttgctc cgacagggga tgtgacaatg gcactctcgc catgggctgg ggttccggca   1800
ccgccaactt cccgtacgtc gtcacgcccg atgccgcgct gcaggcgcag gccctccagg   1860
acggttcgcg ctacgagagc atcctgtcca actatgcgac atcgcaaata aggctcttg   1920 tgtcacaagc caacgtgaca gcaatcgtct ttgtcaacgc cgactcgggc gagggctaca   1980
tcaatgtgga cggaaacatg ggcgaccgga agaacctgac gctgtggaag atggcgacg   2040 cgctggtcaa gaacgtggcc agctggtgct ccaacaccat cgtcgtgatc cattccccgg   2100
gcccggttct gctgaccgag tggtacaaca gccccaacgt taccgctatc ctctgggccg   2160
gtctccccgg ccaagagtcc ggcaactcga tcgccgacgt tctgtacggc agggtcaacc   2220
ctgccgcgcg gtcgccgttc acgtgggggcc caacccgcga gagttacggg accgatgttc   2280
tctacacgcc gaacaacggc aacggcgcgc gcaggacga cttcaccgag ggcgtcttca   2340
tcgactaccg ctactttgac aagaccaact cgtccgtcat ttacgagttc ggccacggcc   2400
tcagctacac cacgtttgag tacagcaaca tccgggtaca gaagtcgaac gcgggcaagt   2460
acgagcccac gacgggcaag acctcgcccg cgcccacctt tggcaacttc tcgaccaacc   2520
tcaaagacta cgtgttcccg agccacgagt tcccttacgt ttacgagtac atctatcctt   2580
acctcaacac gaccgacccc aaggcggcct cgggcgacgc gaactacggc cagacggccg   2640
acaagttcct cccgccgcac gcgaccgact cgtcggccca gccgctgctg cgctcgtcgg   2700
gcaagaactc gccgggcggc aaccggcagt tgtacgacgt catgtacacg atcacggccg   2760
acatcaagaa cacgggctcg atcgtcggcg aggaggtgcc gcagctgtac gtcgcgctgg   2820
gcgggccgga cgaccccaag gtgcagctgc gcgactttga ccgcatccgc atcgacccgg   2880
gcaagacggc gcagttccgc ggcacgctga cccgcaggga cctgagcaac tgggatacga   2940
cgctgcagga ctgggtcatt agcaagtaca agaagacggc gtatgtgggg aggagcagcc   3000
ggaagctgga cttgagcatt gagttgccgt ga                                 3032
```

<210> SEQ ID NO 2
<211> LENGTH: 872
<212> TYPE: PRT
<213> ORGANISM: Thielavia terrestris

<400> SEQUENCE: 2

```
Met Lys Pro Ala Ile Val Leu Ser Ser Leu Ala Cys Ser Gly Leu Ala
1               5                   10                  15

Ala Ala Ser Ala Val Ser Ser Ser Asp Lys Pro Leu Glu Lys Arg Thr
            20                  25                  30

Leu Ala Thr Ser Glu Pro Phe Tyr Pro Ser Pro Trp Met Asn Pro Asp
        35                  40                  45

Ala Asp Gly Trp Thr Glu Ala Tyr Ala Arg Ala Lys Glu Phe Val Ser
    50                  55                  60

Arg Met Thr Leu Leu Glu Lys Val Asn Leu Thr Thr Gly Val Gly Trp
65                  70                  75                  80
```

```
Glu Ala Glu Gln Cys Val Gly Gln Val Gly Ala Ile Pro Arg Leu Gly
                85                  90                  95

Leu Arg Ser Leu Cys Met Gln Asp Ser Pro Leu Gly Val Arg Gly Thr
            100                 105                 110

Asp Phe Asn Ser Gly Phe Pro Ser Gly Gln Thr Ala Ala Ala Thr Phe
        115                 120                 125

Asp Arg Gly Leu Ile Tyr Arg Arg Gly Tyr Ala Met Gly Gln Glu Ala
    130                 135                 140

Arg Gly Lys Gly Val Asn Val Leu Leu Gly Pro Val Ala Gly Pro Leu
145                 150                 155                 160

Gly Arg Ala Pro Thr Gly Gly Arg Asn Trp Glu Gly Phe Ser Pro Asp
                165                 170                 175

Pro Val Leu Thr Gly Val Gly Met Ala Glu Ser Ile Lys Gly Ile Gln
            180                 185                 190

Asp Ala Gly Thr Ile Ala Cys Ala Lys His Phe Ile Gly Asn Glu Gln
        195                 200                 205

Glu His Phe Arg Gln Val Gly Glu Ala Gln Gly Tyr Gly Phe Asn Ile
    210                 215                 220

Ser Glu Ala Leu Ser Ser Asn Ile Asp Asp Lys Thr Leu His Glu Leu
225                 230                 235                 240

Tyr Leu Trp Pro Phe Ala Asp Ala Val Arg Ala Gly Val Gly Ser Val
                245                 250                 255

Met Cys Ser Tyr Gln Gln Leu Asn Asn Ser Tyr Ser Cys Gln Asn Ser
            260                 265                 270

Lys Leu Leu Asn Gly Leu Leu Lys Gly Glu Leu Gly Phe Gln Gly Phe
        275                 280                 285

Val Met Ser Asp Trp Gln Ala Gln His Thr Gly Ala Ala Ser Ala Val
    290                 295                 300

Ala Gly Leu Asp Met Thr Met Pro Gly Asp Thr Glu Phe Asn Thr Gly
305                 310                 315                 320

Arg Ser Tyr Trp Gly Ala Asn Leu Thr Leu Ala Val Leu Asn Gly Thr
                325                 330                 335

Val Pro Ala Tyr Arg Ile Asp Asp Met Ala Met Arg Ile Met Ala Ala
            340                 345                 350

Phe Phe Lys Val Asn Lys Asp Ile Lys Leu Asp Pro Ile Asn Phe Ser
        355                 360                 365

Phe Trp Thr Leu Asp Thr Tyr Gly Pro Ile His Trp Ala Ala Gln Thr
    370                 375                 380

Gly Tyr Gln Gln Ile Asn Tyr His Val Asp Arg Ala Asp His Gly
385                 390                 395                 400

Ser Leu Ile Arg Glu Ile Gly Ala Lys Gly Thr Val Leu Leu Lys Asn
                405                 410                 415

Thr Gly Ser Leu Pro Leu Lys Lys Pro Lys Phe Leu Ala Val Ile Gly
            420                 425                 430

Glu Asp Ala Gly Pro Asn Thr Ser Gly Pro Asn Ser Cys Ser Asp Arg
        435                 440                 445

Gly Cys Asp Asn Gly Thr Leu Ala Met Gly Trp Gly Ser Gly Thr Ala
    450                 455                 460

Asn Phe Pro Tyr Val Val Thr Pro Asp Ala Ala Leu Gln Ala Gln Ala
465                 470                 475                 480

Leu Gln Asp Gly Ser Arg Tyr Glu Ser Ile Leu Ser Asn Tyr Ala Thr
                485                 490                 495

Ser Gln Ile Lys Ala Leu Val Ser Gln Ala Asn Val Thr Ala Ile Val
            500                 505                 510
```

```
Phe Val Asn Ala Asp Ser Gly Glu Gly Tyr Ile Asn Val Asp Gly Asn
            515                 520                 525

Met Gly Asp Arg Lys Asn Leu Thr Leu Trp Lys Asp Gly Asp Ala Leu
530                 535                 540

Val Lys Asn Val Ala Ser Trp Cys Ser Asn Thr Ile Val Val Ile His
545                 550                 555                 560

Ser Pro Gly Pro Val Leu Leu Thr Glu Trp Tyr Asn Ser Pro Asn Val
                565                 570                 575

Thr Ala Ile Leu Trp Ala Gly Leu Pro Gly Gln Glu Ser Gly Asn Ser
            580                 585                 590

Ile Ala Asp Val Leu Tyr Gly Arg Val Asn Pro Ala Ala Arg Ser Pro
        595                 600                 605

Phe Thr Trp Gly Pro Thr Arg Glu Ser Tyr Gly Thr Asp Val Leu Tyr
610                 615                 620

Thr Pro Asn Asn Gly Asn Gly Ala Pro Gln Asp Asp Phe Thr Glu Gly
625                 630                 635                 640

Val Phe Ile Asp Tyr Arg Tyr Phe Asp Lys Thr Asn Ser Ser Val Ile
                645                 650                 655

Tyr Glu Phe Gly His Gly Leu Ser Tyr Thr Thr Phe Glu Tyr Ser Asn
            660                 665                 670

Ile Arg Val Gln Lys Ser Asn Ala Gly Lys Tyr Glu Pro Thr Thr Gly
        675                 680                 685

Lys Thr Ser Pro Ala Pro Thr Phe Gly Asn Phe Ser Thr Asn Leu Lys
690                 695                 700

Asp Tyr Val Phe Pro Ser His Glu Phe Pro Tyr Val Tyr Glu Tyr Ile
705                 710                 715                 720

Tyr Pro Tyr Leu Asn Thr Thr Asp Pro Lys Ala Ser Gly Asp Ala
                725                 730                 735

Asn Tyr Gly Gln Thr Ala Asp Lys Phe Leu Pro Pro His Ala Thr Asp
            740                 745                 750

Ser Ser Ala Gln Pro Leu Leu Arg Ser Ser Gly Lys Asn Ser Pro Gly
        755                 760                 765

Gly Asn Arg Gln Leu Tyr Asp Val Met Tyr Thr Ile Thr Ala Asp Ile
770                 775                 780

Lys Asn Thr Gly Ser Ile Val Gly Glu Glu Val Pro Gln Leu Tyr Val
785                 790                 795                 800

Ala Leu Gly Gly Pro Asp Asp Pro Lys Val Gln Leu Arg Asp Phe Asp
                805                 810                 815

Arg Ile Arg Ile Asp Pro Gly Lys Thr Ala Gln Phe Arg Gly Thr Leu
            820                 825                 830

Thr Arg Arg Asp Leu Ser Asn Trp Asp Thr Thr Leu Gln Asp Trp Val
        835                 840                 845

Ile Ser Lys Tyr Lys Lys Thr Ala Tyr Val Gly Arg Ser Ser Arg Lys
850                 855                 860

Leu Asp Leu Ser Ile Glu Leu Pro
865                 870

<210> SEQ ID NO 3
<211> LENGTH: 46
<212> TYPE: DNA
<213> ORGANISM: Thielavia terrestris
<220> FEATURE:
<221> NAME/KEY: misc_feature
<222> LOCATION: (45)..(45)
<223> OTHER INFORMATION: V=A,C, or G
<220> FEATURE:
```

```
<221> NAME/KEY: misc_feature
<222> LOCATION: (46)..(46)
<223> OTHER INFORMATION: N=A,C,G, or T

<400> SEQUENCE: 3
gactagttct agatcgcgag cggccgccct tttttttttt ttttvn         46

<210> SEQ ID NO 4
<211> LENGTH: 16
<212> TYPE: DNA
<213> ORGANISM: Thielavia terrestris

<400> SEQUENCE: 4
tcgacccacg cgtccg                                          16

<210> SEQ ID NO 5
<211> LENGTH: 12
<212> TYPE: DNA
<213> ORGANISM: Thielavia terrestris

<400> SEQUENCE: 5
cggacgcgtg gg                                              12

<210> SEQ ID NO 6
<211> LENGTH: 17
<212> TYPE: DNA
<213> ORGANISM: Thielavia terrestris

<400> SEQUENCE: 6
gtaaaacgac ggccagt                                         17

<210> SEQ ID NO 7
<211> LENGTH: 19
<212> TYPE: DNA
<213> ORGANISM: Thielavia terrestris

<400> SEQUENCE: 7
aggaaacagc tatgaccat                                       19

<210> SEQ ID NO 8
<211> LENGTH: 20
<212> TYPE: DNA
<213> ORGANISM: Thielavia terrestris

<400> SEQUENCE: 8
atttaggtga cactatagaa                                      20

<210> SEQ ID NO 9
<211> LENGTH: 20
<212> TYPE: DNA
<213> ORGANISM: Thielavia terrestris

<400> SEQUENCE: 9
taatacgact cactataggg                                      20

<210> SEQ ID NO 10
<211> LENGTH: 32
<212> TYPE: DNA
<213> ORGANISM: Thielavia terrestris

<400> SEQUENCE: 10
actggattta ccatgaagcc tgccattgtg ct                        32

<210> SEQ ID NO 11
```

```
<211> LENGTH: 38
<212> TYPE: DNA
<213> ORGANISM: Thielavia terrestris

<400> SEQUENCE: 11
tcacctctag ttaattaatc acggcaactc aatgctca                              38
```